United States Patent [19]

Adams

[11] 3,980,764

[45] Sept. 14, 1976

[54] POLYMERIC COMPETITIVE PROTEIN BINDING ADSORBENTS FOR RADIOASSEY

[75] Inventor: Raymond J. Adams, Anaheim, Calif.

[73] Assignee: Curtis Nuclear Corporation, Los Angeles, Calif.

[22] Filed: Nov. 5, 1973

[21] Appl. No.: 412,918

[52] U.S. Cl. .............................. 424/1; 260/112 R; 424/359
[51] Int. Cl.² ................. A61K 43/00; A61K 39/00; A61K 37/06
[58] Field of Search ............................... 424/1, 359

[56] References Cited
UNITED STATES PATENTS

| | | | |
|---|---|---|---|
| 2,957,808 | 10/1960 | Campbell | 424/12 |
| 3,410,839 | 11/1968 | De Carvalho | 424/12 X |

OTHER PUBLICATIONS

Avrameas et al., "Biologically Active Water–Insoluble Protein Polymers," in The Journal of Biological Chemistry, vol. 242, No. 7, Apr. 10, 1967, pp. 1651–1659.

Primary Examiner—Leland A. Sebastian
Assistant Examiner—Christine M. Nucker
Attorney, Agent, or Firm—Lyon and Lyon

[57] ABSTRACT

Serum protein comprising specific binding proteins such as antibodies, $B_{12}$ intrinsic factor, thyroxin binding globulin and the like may be copolymerized with globulin constituents of serum by the action of ethylchloroformate to form readily packed insoluble precipitates which, following purification as by washing, are eminently suited for employment as competitive binding protein absorbents in radioassay procedures.

10 Claims, No Drawings

POLYMERIC COMPETITIVE PROTEIN BINDING ADSORBENTS FOR RADIOASSAY

BACKGROUND OF THE INVENTION

1. Field of the Invention

This invention relates to serum radioassays and, more particularly, to improved polymeric competitive protein binding adsorbents for use in such assays.

In recent years, radioassay techniques have made possible detection and quantification of circulating levels of serum components present in extremely minute concentrations in blood. Typically in such assays, an unknown quantity of a given serum component is made to compete with a known quantity of a radioactively labeled "marker" substance for a limited number of binding sites on a competitive protein binding adsorbent specific for determinants characteristic of both the unknown and its homologous marker. The resulting complex is isolated from unbound moieties and its radioactivity is measured. A difference between the radioactivity of that complex and one similarly derived from a standard whose content of the substance under assay is known can be directly related to the concentration of unknown in the serum sample assayed.

While a wide variety of specific adsorbent substances may be employed in radioassay procedures, including receptor and other specific binding proteins, e.g., $B_{12}$ intrinsic factor and thyroxin binding globulin, radioassay is most commonly applied to the detection of substances specifically bound by circulating antibodies. In such "radioimmunoassays", an immunogen or hapten under assay competes with homologous marker for binding sites on the antibody, whose radioactivity is then measured. In this context the term "immunogen" denotes any protein, polypeptide, polysaccharide, mucopolysaccharide or other substance, whether or not normally foreign to the circulatory system, which reacts specifically with a given antibody to form an antigen-antibody complex. A "hapten" is a small molecule or portion thereof capable of specifically binding to a given antibody but, by reason of its size, incapable of generating antibodies unless conjugated to an immunogenic carrier.

2. Description of the Prior Art

The isolation of the antigen-antibody complex from the other reactants for the measurement of its radioactivity in radioimmunoassays has been effected in various ways.

According to one procedure employed in radioimmunoassay of digoxin and other sterol-like compounds, as described by Meade and Kleist in *J. Lab. Clin. Med.* 80:748, 1972, the free digoxin was separated from the antibody-bound digoxin by adsorption of the former to dextran-coated charcoal. It was found, however, that a rapid dissociation of the digoxin-antibody complex occurred upon removal of the free digoxin by the dextran-coated charcoal, and that good results therefore were dependent upon a rigidly fixed time of contact with charcoal for all samples. Meade and kleist therefore investigated various methods of precipitating the antibody-bound digoxin to effect irreversible removal of the bound fraction.

Another approach, described by Donini and Donini in *Karolinska Symposia*, Stockholm, 1969, page 257, employed specific antisera made insoluble by polymerization for the separation of bound and free hormone in the radioimmunoassay of follicle stimulating hormone and luteinizing hormone. In their method, antisera were precipitated from aqueous solutions by the addition of ethyl chloroformate according to a modification of a procedure described by Avrameas & Ternynck in *J. Biol. Chem.*, 242:1651 (1967).

According to Donini and Donini, the antisera were sometimes copolymerized with bovine serum albumin (BSA); this procedure being adopted when only a small amount of antiserum was available. For example, 0.2 to 0.5 ml of antiserum was brought to 2 ml by the addition of an appropriate amount of acetate buffer, pH 5.0, containing BSA in such a quantity that the final protein concentration amounted to 35 to 50 mg/ml. According to the authors, this copolymerization procedure was feasible only when the antiserum was used at a high dilution.

SUMMARY OF THE INVENTION

According to the present invention, specific binding proteins are copolymerized with certain serum proteins to form insoluble adsorbents for complementary specific immunogens or haptens. The adsorbents thus produced are primarily useful as such in conventional radioassays of sera.

The present invention is based upon the discovery that globulin constituents of serum, particularly gamma globulins, when copolymerized with any of a wide range of specific antisera or other specific binding proteins produce insoluble precipitates which may be tightly packed by centrifugation, thus facilitating separation from liquid by decantation of the latter. [While for the sake of convenience reference is made herein to copolymerization with "antisera", (serum enriched by challenge in a particular antibody), it should be understood that it is the proteinaceous component of antisera which engages in the copolymerization reaction. Typically, antisera contains from about 4 to about 8 percent by weight protein, and most commonly contains on the order of about 7 percent by weight protein.]

Thereafter, the same packing characteristic of the precipitated copolymer facilitates washing, usually with a suitable buffer, followed by further centrifugation and separation from the liquid of the washed polymer by means such as, for example, aspiration or filtration.

The solid insoluble copolymer then may be put into any convenient form for subsequent use as an adsorbent in radioimmunoassays of the character hereinbefore described, where its superior packing characteristic is of further advantage in facilitating separation of bound and unbound marker.

Additional advantage may be expected to accrue from use of globulin as comonomer, as distinguished from the albumin comonomer to which resort has heretofore been had, viz., diminished cross-reactivity with substances other than that under assay. Thus, while I do not wish to be bound by any theory, globulin constituents of serum, such as gamma globulin, appear to exhibit substantially less nonspecific or cross reactivity than is characteristic of serum albumin.

DESCRIPTION OF THE PREFERRED EMBODIMENTS

Globulin constituents may be isolated by several techniques, e.g., ultracentrifugation or agar electrophoresis, but generally classic Cohn low temperature-alcohol procedures are employed to obtain the basic fractions. Gamma, beta, and alpha globulins predominate, respectively, in Cohn Fractions II, III and IV.

Cohn Fraction II typically contains on the order of 95% gamma globulins and may be subjected to further purification by the precipitation of contaminants (largely beta globulins), as by the process described in U.S. Pat. No. 3,382,227, so that the resulting product contains, e.g., more than about 99% gamma globulin. Fraction II may be separated by other techniques, such as DEAE ion exchange, into the immunoglobulins 7 S gamma globulin (IgG), 19 S gamma globulin (IgM), and gamma A globulin (IgA) and other fragments which may be characterized by immunoelectrophoretic or acrylamine gel techniques, sedimentation constants, or other physical-chemical methods.

Globulin proteins which have been discovered to produce copolymers having especially superior properties when copolymerized with any of a wide range of specific binding proteins are those contained in Cohn Fraction II of the blood proteins, especially those known as the 7 S gamma globulins; there being, however, a number of synonyms for this appellation as shown by the table appearing at pages 180 and 181 of *Molecular Biology of Human Proteins* by H. J. Muller-Eberhard and J. F. Heremans, Elsevier Publishing Co., New York, 1966, Vol. 1, Section II, Chapter 1. The 7 S gamma globulins are reported to have molecular weights in the range of approximately 150,000 to 161,000.

The copolymer resulting from ethylchloroformate polymerization may contain, e.g., up to 50 percent by weight covalently bound specific binding protein co-monomer (because, in the case of immunoadsorbent copolymers, the specific binding protein may itself comprise gamma globulin, the copolymer is, herein, characterized not by reference to total globulin content but rather by the contribution of each reagent comonomer to the copolymer as a whole). Most commonly, the copolymer comprises a minor radioassay effective proportion of covalently bound specific binding protein comonomer, the globulin comonomer predominating. Preferably, the copolymer comprises on the order of about 7 percent by weight or less of the former constituent.

Following workup, the copolymer is preferably combined with a vehicle comprising, e.g., filler, lubricant, buffer constituents, disintegrants and other conventional bioactively inert tabletting addends and formed to tablets of 20–50 mg, most commonly 30 mg. Normally, the copolymer content of such tablets is less than about 1 percent, commonly less than 0.2 percent, and most preferably in the range from about 0.01 to about 0.1 percent by weight.

While conventionally in radioassay a radioactive marker is separately supplied in liquid form, it may in fact itself be tabletted, advantageously together with competitive binding protein such as antibody or the like. In the latter event care must be taken to prevent premature binding between marker and, e.g., antibody, i.e., binding prior in time to wetting with buffer, water, saline, etc.

Thus, minor effective radioassay amounts of the radioactive marker may be combined with powder lubricant, powder diluent or the like before drying and blending the same with the copolymer heretofore described.

The amount of cross-reactive radioactive marker employed is a function of the optimal measureable range of proportions in serum of the substance under assay, and usually approximates the lower end of that range. For example: to assay a 0.05 ml serum sample for a substance optimally measureable when present in serum in the range from about 1 to about 10 micrograms per ml, 0.05 micro grams radioactive marker may be employed. It will be appreciated that this aspect of my invention finds application not only in the case of the copolymers heretofore described, but indeed in every instance in which specific binding protein is made up in discrete solid measures (e.g., capsule, tablet, etc.) for radioassay employments.

In the examples given hereinafter certain buffers, etc. are used in one or more examples and therefore are described preliminarily.

1. A PSB buffer was prepared by dissolving 9.028 grams of potassium phosphate mono-basic per liter of deionized water and, separately, 9.514 grams of sodium phosphate dibasic per liter of deionized water. These two solutions were then combined in a ratio of 7 parts of the sodium phosphate solution to 3 parts of the potassium phosphate solution, and sodium chloride was added in the amount of 9.0 grams per liter of buffer.

2. A 1.0 M Tris buffer was prepared by dissolving 121 grams of tromethamine (2-amino-2 hydroxymethyl-1, 3 propanediol) per liter of deionized water and adjusting the pH to 7.2 using 6 N HCl.

3. A 0.1 M Tris buffer was prepared by diluting the above 1.0 Tris buffer with deionized water in the ratio of 1:10.

4. A 0.1 M Tris—0.2% albumin buffer was prepared by dissolving 2.0 grams of bovine serum albumin per liter of the above 0.1 M Tris buffer.

5. a homogenizing wash of 0.1% sodium carbonate was prepared by dissolving 1.0 gram of sodium carbonate per liter of deionized water.

Herein, all parts and percentages are by weight, unless otherwise specified.

EXAMPLE I

Insulin antibody polymer tablets prepared by the following procedure.

Human gamma globulin, Cohn Fraction II, was added to a beaker containing 10 ml of PBS buffer per gram of gamma globulin and the solution was mixed for 60 minutes to dissolve the globulin. The mixture was then centrifuged and the solution was decanted into a beaker.

To this solution insulin guinea pig antisera (Alpha Gamma Laboratories, Sierra Madre, California) was added in the proportion of 2 ml per gram of gamma globulin, and the pH was adjusted to 5.0 with 1N HCl.

To effect copolymerization of the antisera and gamma globulin the beaker was then transferred to a hood and ethyl chloroformate (Baker Grade) was added, dropwise while stirring, in the proportion of 0.6 ml per milliliter of insulin antisera. After mixing for one hour the pH was readjusted to 5.0 with 1 N sodium hydroxide and after further mixing for an additional 2 hours, the pH was adjusted to 7.0 with 1 N sodium hydroxide. The mixture of precipitate and supernatant was then transferred to a centrifuge tube and centrifuged at 3000 RPM for 10 minutes, after which the supernatant was decanted.

The copolymer residue constituting the precipitate was washed with the 1.0 M Tris buffer by thorough slurrying and centrifuging and homogenized with the 0.1% sodium carbonate wash after which it was again centrifuged and the supernatant discarded.

The copolymer residue was then washed twice with 1.0 M Tris buffer and 4 times with the 0.1 M Tris buffer, following which the optical density of the supernatant was read at 280 m$\mu$. If an optical density greater than 0.15 was read, washing with 0.1 M Tris buffer was continued until the optical density was read at 0.15 or less.

Using 20 of the 0.1 M Tris—0.2% albumin buffer per milliliter of antisera, the copolymer residue was washed into a mortar and pestle and slurried. A powder diluent (lactose) was then added slowly with mixing, in the proportion of 65 grams powder diluent per milliliter of antisera, and the mixture was triturated thoroughly. The resulting copolymer diluent paste was dried under vacuum and passed through a 100 mesh sieve.

The resulting powder blend was placed in a beaker and 6.0 ml of deionized water per 50 grams of powder blend was added. The mixture was triturated to uniformly dampen the powder following which it was forced through a 40 mesh sieve and the resulting granules were collected on an absorbent towel.

The granules were then placed in a sieve pan and a powder lubricant, prepared by milling in a micro mill rice starch to which 2% sodium stearate has been added, was mixed with the granules in the proportion of 40 grams of powder lubricant per 100 grams of granules. The pan was shaken vigorously to uniformly coat the granules with lubricant and they were then forced through a 30 mesh sieve. The coated granules were dried under vacuum, again forced through a 30 mesh sieve and collected on an 80 mesh sieve to remove the excess powder.

Tablets containing amounts of diluted copolymer giving optimal absorption without sacrificing sensitivity were then formed and employed as immunoadsorbents in radioimmunoassays of the character described above.

EXAMPLE II

Human growth hormone (HGH) antibody polymer tablets were prepared by the following procedure.

A solution of human gamma globulin, Cohn Fraction II, was prepared as described in Example I, and to it HGH goat antisera (Alpha Gamma Laboratories, Sierra Madre, California) was added in the proportion of 1 ml per gram of gamma globulin. The pH was then adjusted to 5.0 with 1 N HCl.

Copolymerization of the antisera and gamma globulin was then effected in the same manner as described in Example I, using 0.6 ml of ethyl chloroformate per milliliter of HGH goat antisera; the precipitated copolymer being isolated and homogenized with the several buffers and wash as described in Example I until a supernatant optical density of 0.15 or less at 180 m$\mu$ was achieved.

Using 40 ml of the 0.1 M Tris—0.2% of albumin buffer per milliliter of HGH goat antisera, the copolymer was washed into a mortar and slurried. A powder diluent of 100 grams of lactose per milliliter of antisera was then added slowly with mixing, and the mixture was thoroughly triturated. The copolymer/diluent paste was dried under vacuum and passed through a 100 mesh sieve to insure a uniform blend, whereafter 6 ml of deionized water per 50 grams of lactose was added. The mixture was triturated to uniformly dampen the powder and forced through a 40 mesh sieve after which the resulting granules were dried under vacuum.

The granules were then forced through a 30 mesh sieve and collected on an 80 mesh sieve. They were then placed in a sieve pan to which was added, with shaking of the pan, a powder lubricant earlier prepared by milling, in a micro mill, rice starch to which had been added 2% sodium stearate. Powder lubricant is employed in an amount sufficient to coat all granules thoroughly. The granules were then placed on an 80 mesh sieve and shaken lightly to remove excess powder.

Tablets containing an amount of the diluted copolymer giving optimal absorption without sacrificing sensitivity were then formed and employed as immunoadsorbents in radioimmunoassays of the character described above.

EXAMPLE III

Digoxin antibody polymer tablets were prepared by the following procedure.

A solution of human gamma globulin, Cohn Fraction II, was prepared as described in Example I, and to it digoxin rabbit antisera (Conrose Associates, San Diego, California) was added in the proportion of 0.1 ml of antisera per 5.0 grams of gamma globulin. The pH was then adjusted to 5.0 with 1 N HCl.

Copolymerization of the antisera and gamma globulin was then effected under a hood by adding ethyl chloroformate (Baker grade), dropwise while stirring, in the proportion of 4.0 ml per 0.1 milliliter of digoxin antisera. After mixing for two hours, the pH was adjusted to 7.0 with 1 N sodium hydroxide. The mixture of precipitate and supernatant was then transferred to a centrifuge tube and centrifuged at 3000 r.p.m. for 10 minutes after which the supernatant was decanted.

The copolymer residue constituting the precipitate was then washed and homogenized with the several buffers and washed as described in Example I until a supernatant optical density of 0.15 or less at 280 M$\mu$ was achieved.

Using 160 ml of water per 0.1 ml of antisera the copolymer was washed into a mortar and pestle and slurried. A powder diluent composed of, proportionately, 18.25 grams $Na_2HPO_4$, 4.375 grams $KH_2PO_4$, and lactose, AR, 450 grams was then added in the proportion of 450 grams per 0.1 ml of antisera, the addition being effected slowly with mixing and the mixture thoroughly triturated.

The mixture was then dried under vacuum, with occasional mixing until completely dry.

The powder was then forced through a 100 mesh sieve to insure a uniform blend and 6 ml of deionized water per 50 grams of lactose was added. The mixture was triturated to thoroughly dampen the powder, forced through a 40 mesh sieve, and the granules were collected in a sieve pan.

A powder lubricant was prepared by milling in a micro mill rice starch, to which 2% sodium stearate had been added, and was mixed with the granules in the proportion of 40 grams of powder lubricant per 100 grams of granules. The pan was shaken vigorously to uniformly coat the granules with lubricant and they were then forced through a 30 mesh sieve. The coated granules were dried under vacuum, again forced through a 30 mesh sieve and collected on an 80 mesh sieve to remove the excess powder.

Tablets containing amounts of diluted polymer giving optimal absorption without sacrificing sensitivity were then formed and employed as immunoadsorbents in radioimmunoassays of the character described above.

EXAMPLE IV

Digitoxin antibody polymer tablets were prepared by the following procedure.

A solution of human gamma globulin, Cohn Fraction II, was prepared as described in Example I, and to it digitoxin antisera (Wien Laboratories, Succasunna, New Jersey) was added in the proportion of 2.0 ml per 6.0 grams of gamma globulin. The pH was then adjusted to 5.0 with 1 N HCl.

Copolymerization of the antisera and gamma globulin, and separation, washing and homogenizing of the precipitated copolymer was then effected in the same way as has been described in Example III except that, for the copolymerization step, the ethyl chloroformate was added in the proportion of 3.0 ml per 1.0 ml of digitoxin antisera.

After washing the copolymer until a supernatant optical density of 0.15 or less at 280 M$\mu$ was achieved, the material was process in the same way as has been described in Example III, save that powder diluent was added in the proportion of 35 gms/ml antisera, and tablets containing amounts of diluted polymer giving optimal absorption without sacrificing sensitivity were then formed and employed as immunoadsorbents in radioimmunoassays of the character described above.

EXAMPLE V

Vitamin $B_{12}$ Intrinsic Factor polymer tablets were prepared by the following procedure.

A solution of human gamma globulin, Cohn Fraction II, was prepared as described in Example I, and to it $B_{12}$ Intrinsic Factor (Nutritional Biochemicals, Co., Inc., Cleveland, Ohio) was added in the proportion of 10.0 mg per 4.0 grams of gamma globulin. The pH was then adjusted to 5.0 with 1 N HCl.

Copolymerization of the Intrinsic Factor and gamma globulin, and separation, washing and homogenizing of the precipitated copolymer was then effected in the same way as has been described in Example III, except that, for the copolymerization step, the ethyl chloroformate was added in the proportion of 2.0 ml per 10 mg of Intrinsic Factor.

After washing the copolymer until a supernatant optical density of 0.15 or less at 280 m$\mu$ was achieved, 12 ml of water per 10 mg of Intrinsic Factor were used to wash the copolymer into a mortar where it was slurried, mixed with 60 grams of lactose per 10 mg of Intrinsic Factor and thoroughly triturated. The mixture was then dried under vacuum with occasional mixing until completely dry, and forced through a 100 mesh sieve to insure a good blend.

The powder was then placed in a beaker and 6 ml of deionized water per 50 grams of lactose was added. The mixture was triturated until the powder was uniformly dampened. It was then forced through a 40 mesh sieve, forming granules which were collected in a sieve pan.

To the granules there was then added 20 grams per 60 grams of lactose of a powder lubricant composed of dextrin to which 2% of sodium stearate had been added; the pan being then shaken until all granules were well coated. After drying the granules under vacuum until completely dry, they were passed through a 30 mesh sieve and collected on a 100 mesh sieve to remove the excess powder.

Tablets containing an amount of the diluted copolymer giving optimal absorption without sacrificing sensitivity were then formed and employed as competitive protein binding absorbents in radioassays of the character described above.

I claim:

1. A tablet useful in radioassay for detecting the presence of a serum constituent comprising in minor effective radioassay proportion a specific adsorbent for said serum consituent comprising a copolymer of globulin and, as a comonomer, a specific binding protein for said serum constituent.

2. A tablet according to claim 1 which additionally comprises a minor radioassay effective proportion of a radioactive marker competitive with said constituent in binding to said protein.

3. A tablet according to claim 1 wherein said specific binding protein comonomer comprises $B_{12}$ intrinsic factor and wherein said globulin is 7 S gamma globulin.

4. A tablet according to claim 1 wherein said adsorbent is a radioimmunoadsorbent.

5. A tablet according to claim 1 wherein said adsorbent is a radioimmunoadsorbent and wherein said globulin is gamma globulin.

6. A tablet according to claim 1 wherein said globulin is 7 S gamma globulin and wherein said specific binding protein comonomer comprises antibody to one of the group consisting of insulin, human growth hormone, digoxin and digitoxin.

7. A tablet according to claim 6 which additionally comprises a minor radioassay effective proportion of a radioactive marker competitive with said constituent in binding to said protein.

8. A specific adsorbent useful for detecting by radioassay the presence of vitamin $B_{12}$ comprising a copolymer of globulin and a protein comonomer comprising vitamin $B_{12}$ intrinsic factor, the latter comonomer being employed in effective radioassay amount.

9. An adsorbent according to claim 8 wherein said globulin is gamma globulin.

10. A specific adsorbent useful for detecting by radioassay an antigen selected from the group consisting of insulin, human growth hormone, digoxin and digitoxin comprising a copolymer of globulin and a protein comonomer selected from the group consisting of the antibodies to insulin, human growth hormone, digoxin and digitoxin, the latter comonomer being employed in effective radioassay amount.

* * * * *